United States Patent [19]
Haverstock

[11] Patent Number: 6,007,564
[45] Date of Patent: Dec. 28, 1999

[54] SKIN CLOSURE DEVICE FOR SURGICAL PROCEDURES

[76] Inventor: Charles B. Haverstock, 44 Frederick La., Glendale, Mo. 63122

[21] Appl. No.: 09/035,713

[22] Filed: Mar. 5, 1998

[51] Int. Cl.$^6$ ..................................................... A61B 17/00
[52] U.S. Cl. ............................................................. 606/216
[58] Field of Search ..................... 606/213, 215, 606/216; 602/41–43, 48, 52–59

[56] References Cited

U.S. PATENT DOCUMENTS

| | | | |
|---|---|---|---|
| 2,196,296 | 4/1940 | Flynn | 606/215 |
| 3,698,395 | 10/1972 | Hasson . | |
| 3,863,640 | 2/1975 | Haverstock . | |
| 3,933,158 | 1/1976 | Haverstock . | |
| 3,971,384 | 7/1976 | Hasson . | |
| 4,038,989 | 8/1977 | Romero-Sierra et al. . | |
| 4,114,624 | 9/1978 | Haverstock . | |
| 4,370,981 | 2/1983 | Sanderson | 606/213 |
| 4,423,731 | 1/1984 | Roomi | 606/216 |
| 4,467,805 | 8/1984 | Fukuda . | |
| 4,531,521 | 7/1985 | Haverstock . | |
| 4,598,004 | 7/1986 | Heinecke . | |
| 4,732,146 | 3/1988 | Fasline et al. . | |
| 4,825,866 | 5/1989 | Pierce . | |
| 4,881,546 | 11/1989 | Kaessmann . | |
| 4,917,112 | 4/1990 | Kalt . | |
| 4,966,605 | 10/1990 | Thieler . | |
| 4,976,726 | 12/1990 | Haverstock . | |
| 5,009,663 | 4/1991 | Brommé . | |
| 5,106,384 | 4/1992 | Polski . | |
| 5,176,703 | 1/1993 | Peterson . | |
| 5,562,705 | 10/1996 | Whiteford | 606/215 |

*Primary Examiner*—Michael Buiz
*Assistant Examiner*—Vikki Trinh
*Attorney, Agent, or Firm*—Haverstock, Garrett and Roberts

[57] ABSTRACT

A skin closure device made of flexible material adhesively attachable to the skin of a person who is preparing to undergo surgery, the device including optional non adhesive areas along opposite sides of an incision and bridging members adapted to engaged the skin closure member on opposite sides of the incision to hold the skin closure member closed against the skin surface adjacent to the incision. The subject invention is also directed to the use of a surgical drape having a window opening through which or in which the subject skin closure can be positioned, the subject skin closure being removable from the window at the conclusion of surgery so that the skin closure device with remain attached to the skin for as long as desired and the surgical drape can be removed for use elsewhere. The subject invention also contemplates attaching a medicated strip extending along the skin closure device in the area of the incision to provide medication help at the conclusion of surgery.

15 Claims, 5 Drawing Sheets

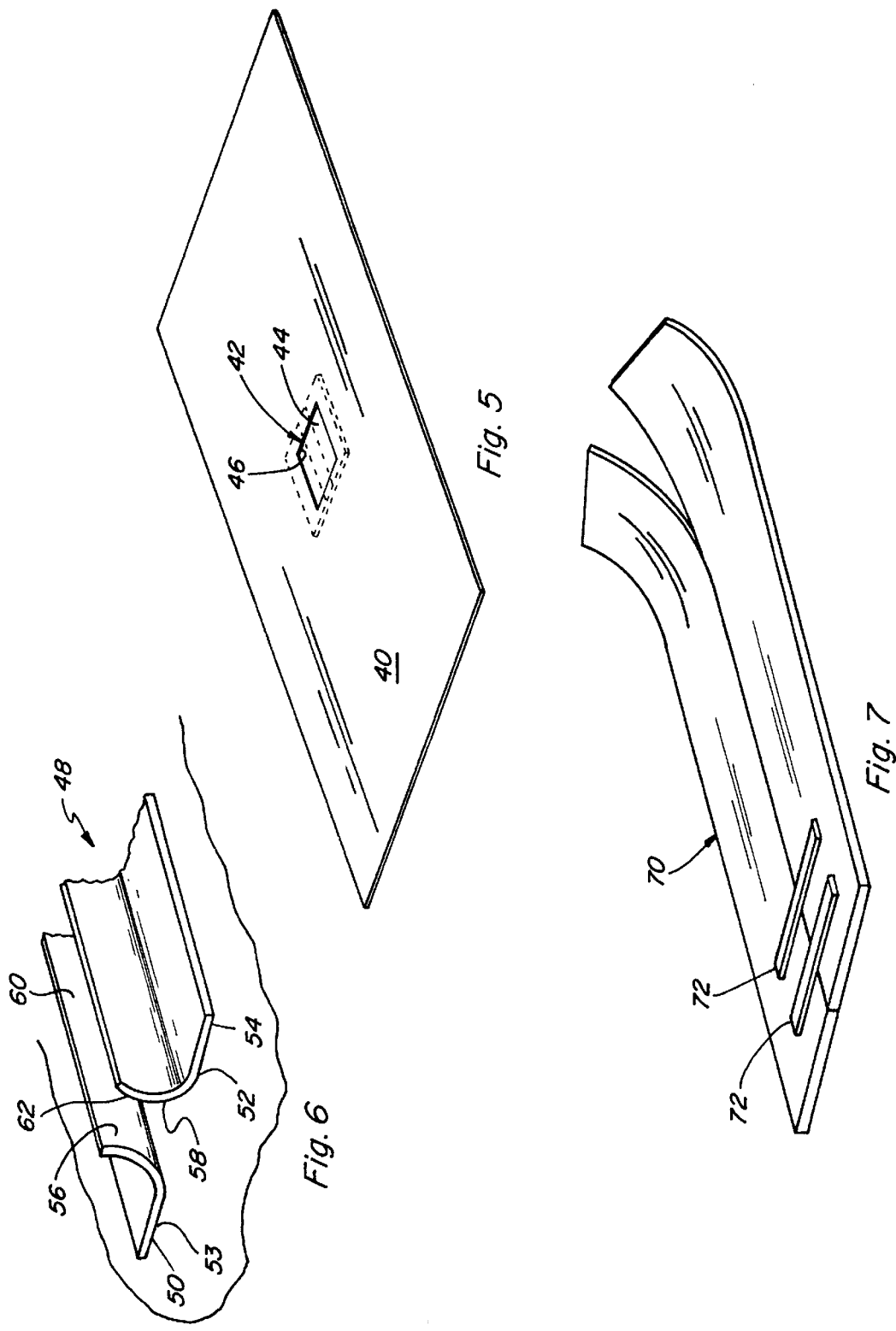

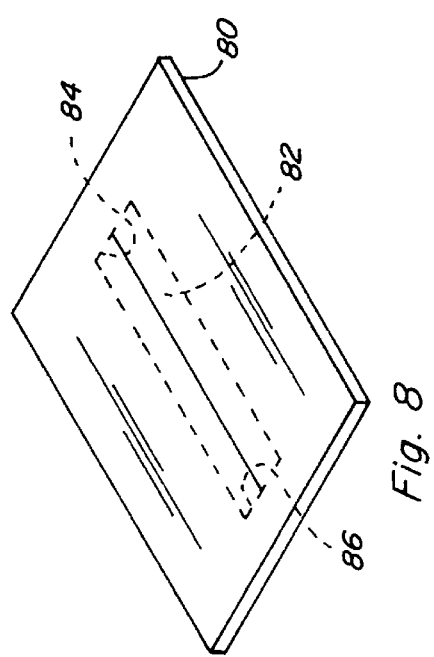
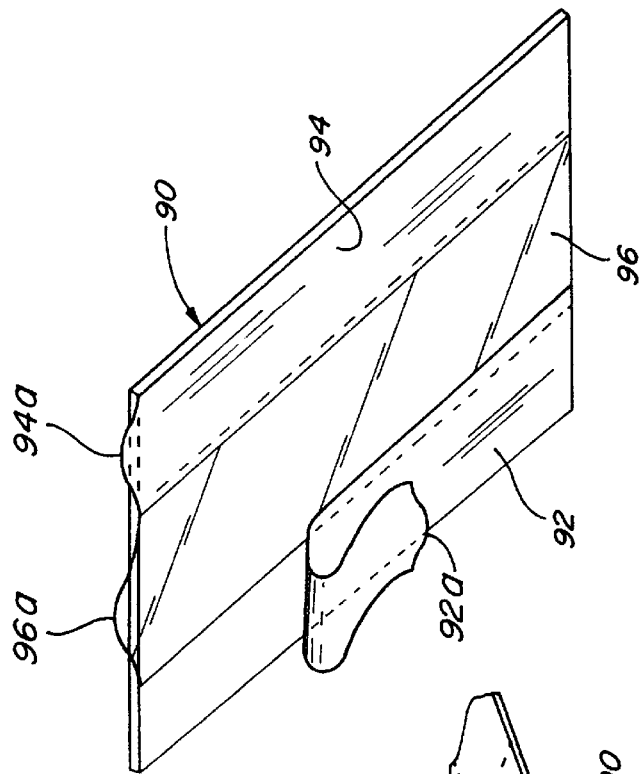
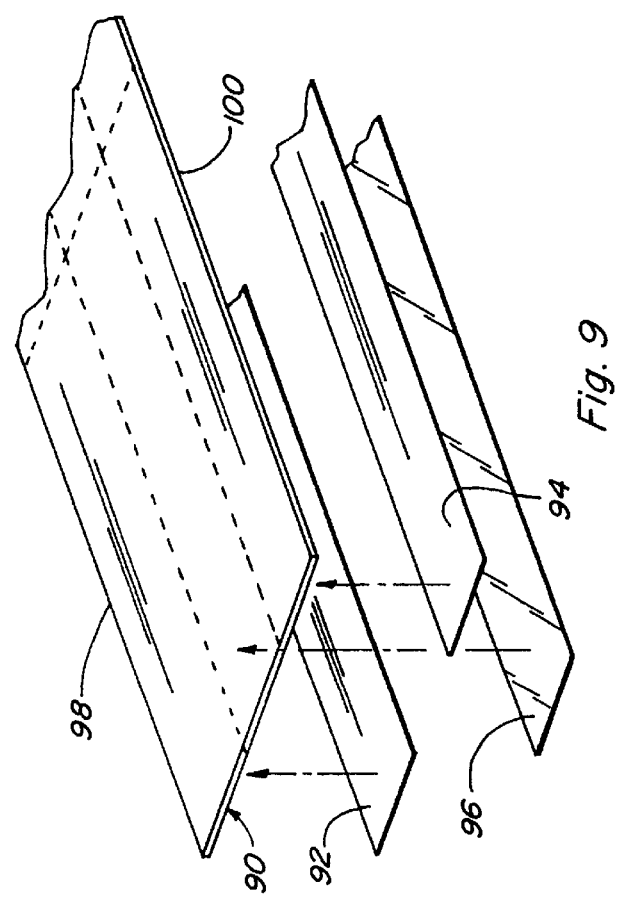

6,007,564

1

SKIN CLOSURE DEVICE FOR SURGICAL PROCEDURES

The present invention constitutes an important advance and improvement over the constructions shown in prior U.S. Pat. Nos. 3,863,640, 3,933,158, 4114,624, 4,531,521 and 4,976,726. The construction shown in the last to issue of Applicant's patents is the closest construction to the present device but has disadvantages that are overcome by the present device. For example, the prior device is adhesively attached to the skin over the whole area of the skin closure device and therefore, when the incision is made by cutting through the member, any stretching or pulling will produce a stretching and pulling difference between the skin closure device and the adjacent skin and this can result in body fluids filling the cracks and crevasses in the device especially in the areas adjacent to the incision, and this can make for an unsightly appearance, possible infection and can possibly result in slowing down the healing process. These disadvantages are overcome by the present construction which has a non-adhesive portion which extends along the incision on both sides and therefore has a folding back ability which means that once the surgery is completed or even during the surgery, the surgeon can clean the area along the incision as required without having to stretch or pull the portion of the skin closure device that is attached to the skin. This has important advantages over what has been done before.

The present invention resides in a skin closure device which is relatively easy to use, provides greater access to the skin of the patient in the area where an incision is to be made or has been made, and it also provides the surgeon with the ability to locate the bandage accurately before it is even attached to the skin by for example, making a line on the skin where the incision is to be made and making a corresponding line on the portion of the skin closure device that does not have adhesive on it so that the surgeon can align the two lines adjacent one other before making the incision. Thereafter when the incision has been made the portions of the skin closure device adjacent opposite sides of the incision will not be adhesively attached to the skin and therefore can be moved or folded back for cleaning purposes or for other purposes or for other purposes including for helping the healing process by not adhesively attaching anything to the skin adjacent to the incision. This also means that surgical staples, sutures or the like can also be used by attaching to the skin where necessary. The subject construction also makes it possible after the incision is closed by means of adhesive bridging members to have a strip with medication in it attached along the area of the incision.

The present construction also lends itself to use with a surgical drape which is a sheet of material that is spread over the body of the person being operated on. The surgical drape has a window which is located in the area where the surgery is to take place. The subject skin closure device can be attached to the surgical drape prior to or after the surgical drape is positioned on the patient and various means can be used to make this attachment. For example, the subject skin closure means can be attached using VELCRO, hook and loop fasteners, it can be attached by zipper means or snap fastener means, it can even be attached integrally with the surgical drape, and it can be attached to the body of the patient prior to applying the surgical drape to the patient. When the surgery has been completed and the skin closure means are closed, the surgical drape can be removed as by disconnecting it from the skin closure means. This can be done by cutting it loose, unzipping it, separating the VELCRO, the hook and loop fasteners or unsnapping it. It can therefore be seen that the present device offers the surgeon many different options for surgery, all of which are easily performed and easily understood.

It is an object of the present invention to provide improved means for closing an incision.

Another object is to enable a surgeon to clean the skin area adjacent to an incision prior to closing the incision.

Another object is to provide a skin closure device that is particularly well suited to surgery and which enables the surgeon to clean the wound area without having to pull anything that is adhesively attached to the skin.

Another object is to enable any length of a skin closure device to be used and enable the surgeon to cut off as much or as short a skin closure device as is necessary for a particular procedure.

Another object is to provide relatively inexpensive easy to use means for closing an incision.

Another object is to give a surgeon more options as to how to close an incision made during surgery.

Another object is to enable a surgeon to close a skin opening in a manner that will be more comfortable and better looking than has been possible heretofore.

Another object is to enable a surgeon to bring the skin edges adjacent opposite sides of an incision into alignment while retaining the skin portions adjacent to the incision in a more comfortable aligned condition.

These and other objects and advantages will become apparent after considering the following detailed specification covering preferred embodiments of the present invention in conjunction with the accompanying drawings wherein:

DESCRIPTION OF THE DRAWINGS

FIG. 5 is a perspective view showing the subject skin closure device extending across an opening in a surgical drape;

FIG. 6 is a view similar to FIG. 3 showing the non-adhesive portions of the skin closure device adjacent opposite sides of the incision being raised and/or folded back to enable cleaning the skin and closure device prior to closing the incision;

FIG. 7 shows an embodiment of the present device having another form of flexible adhesive strips for closing the incision;

FIG. 8 show an embodiment of the subject skin closure device wherein the area where an incision is to be made is surrounded by an adhesive area;

FIG. 9 shows an embodiment wherein the portion of the device that extends around the location where the incision is to be made is covered with a removable non-adhesive layer;

FIG. 10 is a view similar to FIG. 9 but showing the non-adhesive layer around where the incision is made being peeled off of the skin closure device to enable the device to be adhesively attached to the body even extending up to the opposite sides of the incision;

DETAILED DESCRIPTION OF PREFERRED EMBODIMENTS

Figure 1:
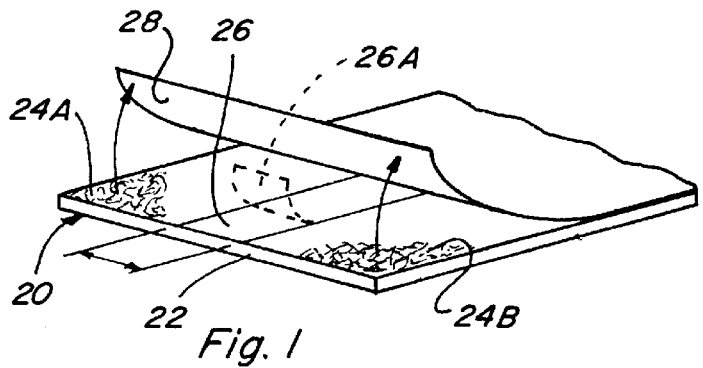
FIG. 1 is a fragmentary perspective view showing one embodiment of the present skin closure device.

Referring to the drawings more particularly by reference numbers, number 20 in FIG. 1 refers to a skin closure device constructed according to the teachings of the present invention. The skin closure device 20 includes a flexible sheet member 22, that has adhesive areas 24A and 24B on one side surface. In the construction as shown in FIG. 1, the adhesive areas 24A and 24B extend to adjacent opposite sides of a non-adhesive area 26 which is positioned between the adhesive areas 24A and 24B along the length of the device. A cover member 28 is shown adhesively attached to the member 22 by means of the adhesive areas 24A and 24B. The closure member 28 is removed from the device 20 prior to use by applying it to the surface of the skin of a person such as a person who is to undergo surgery. Accurately locating the subject device on the skin is important to most surgical procedures as will be explained. The member 22 should preferably be relatively flimsy to conform to the contours of the skin.

Figure 2:
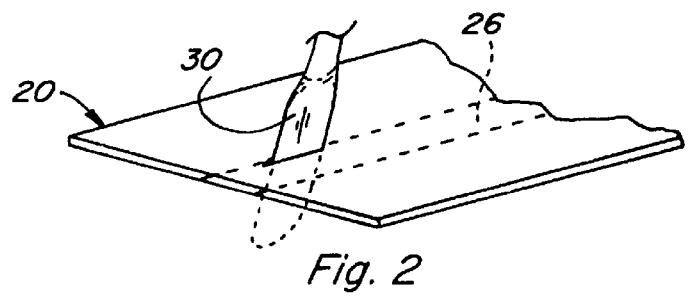
FIG. 2 is a perspective view showing the device of FIG. 1 attached to a body in position for making a surgical incision.

Referring to FIG. 2 it can be seen that the subject closure device 20 has the cover member 28 removed and the adhesive portions areas 24A and 24B are positioned to be placed on the skin of the person to be operated on with the non-adhesive area 26 positioned such that the incision to be made by the scalpel 30 can be made through the non-adhesive portion thereby leaving an area adjacent to each opposite side of the incision where the member 22 is not adhesively attached to the skin.

Figure 3:
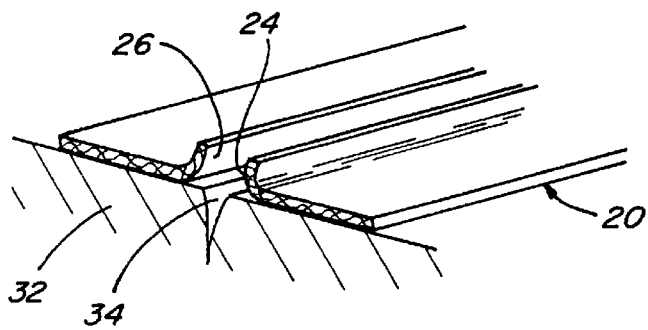
FIG. 3 is a perspective view showing the portions of the skin closure member that extend along opposite sides of the incision being drawn or pulled back to enable the areas adjacent to the incision and the corresponding portions of the skin closure device to be cleaned.

FIG. 3 shows the subject embodiment 20 after the incision has been made with the non-adhesive areas 26 shown raised off the skin 32 along the incision 34 so that the areas adjacent to the incision are not subject to being restrained by the adhesive. This makes for less pulling of the skin by the member 20 and enables the surgeon to better control the operation in a manner more like usual surgery made directly into the skin and not through a skin closure device such as the present device. This also enables the surgeon to move the skin more easily without stressing the skin or the skin closure, and the width of the non-adhesive portion 26 can be varied depending upon the type of surgery to be performed and the amount of unrestrained movement of the skin that is desired. Once the surgery has been completed, the surgeon can again move the portions of the skin closure along opposite sides of the non-adhesive area 26 to a folded back condition so that the skin along opposite sides of the incision and along the non-adhesive portion 26 can be cleaned prior to closing the incision. In the folded back condition it is also possible for the surgeon to apply staples or sutures, subcutaneously or at the surface of the skin, to further close the incision prior to closing the subject skin closure over the incision. If desired, the non-adhesive portion 26 can be formed by attaching a member such the dotted member 26A (FIG. 1) that is non-adhesive but is adhesively attached to the member 22 in the area between the adhesive areas 24A and 24B and can optionally be removed at the conclusion of surgery so that the surgeon can if desired adhesively attach the entire surface of the member 22 to the skin even extending up to the edges of the incision.

Figure 4:
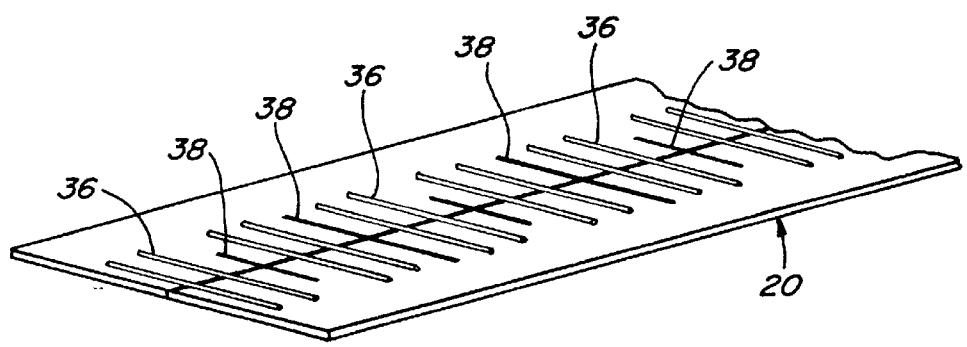
FIG. 4 is a view showing the edges of the skin closure device extending along opposite sides of the incision being held together by elongated adhesive strips.

Once the surgery has been completed and it is time to close the incision, the non-adhesive surface area 26 can be moved downwardly adhesively or non-adhesively as desired into engagement with the skin, and the opposite edges of the incision and the skin closure device can be brought together and held together by means such as by adhesive strips 36 which are strips of a plastic or plastic-like material with an adhesive on them. One form of the strips 36 is shown in FIG. 4. Markings 38 on the device can also be aligned during closure to improve the result.

One of the advantages of using strips 36 or like members including others that will be described later, is that there will be some spaces provided between the adjacent adhesive members 36 and the surface of the closure member 22 along the incision 34, and these spaces enable a member such as a foam member with a medication in it to be adhesively attached to the device along the incision so that the medication can seep into the space between the skin closure member and the incision to prevent infection and to aid the healing process. Such a strip is disclosed in U.S. Pat. No. 4,976,726.

FIG. 5 shows another way to use the subject device which has certain advantages that have been accepted in modern day surgery. FIG. 5 shows a flexible surgical drape 40 with an opening 42 at an intermediate location where surgery is to take place. The surgical drape protects the body of the patient and also provides the window 42 into which, or beneath which, or above which, the subject skin closure device can be positioned and attached if desired. The drape prevents the spread of body fluids about the patient's body and also provides some protection for the subject skin closure device. The manner in which the skin closure device is attached or installed in the window 42 can be as described above and at the conclusion of surgery when the incision has been closed, the surgical drape 40 can be removed and/or detached leaving the patient in a clean, yet surgically correct, condition.

FIG. 6 shows an embodiment 48 of the present device wherein two separate portions 50 and 52 of the subject skin closure device are adhesively attached to the skin 53 prior to surgery. The incision is made between them so that when the surgery is completed the two members can be brought together into adjacent or substantial alignment with the edges of the incision. The members 50 and 52 have adhesive portions 53 and 54 similar to the portions 24A and 24B which are attached to the skin and non-adhesive portions 56 and 58 which are not adhesively attached to the skin. The portions 56 and 58, as in the previous example, can be formed by having non-adhesive cover members 60 and 62 which can be removed to enable them to be adhesively attached to the skin along opposite sides of the incision, if desired.

FIG. 7 shows an embodiment 70 of the subject device which is similar to the embodiment 20 shown in FIGS. 1–4 but uses elongated flexible closure straps 72 which are flat straps with an adhesive on one side surface and a non-adhesive opposite surface. Except for this difference, the construction shown in FIG. 7 is similar to and is used similarly to the constructions described above.

FIG. 8 shows an embodiment wherein the closure member 80 has an adhesive covering the lower surface except for the outlined area 82 which may be non-adhesive or may be a non-adhesive member attached adhesively to the surface of the member 80 at the location shown. With this construction, the incision (not shown), which may be short, can be made through the member 80 in non-adhesive area 82 but generally will not extend across the full length of the member 80. This construction enables the portion of the non-adhesive area 82 to be slit at an angle adjacent opposite ends of the incision as at 84 and 86 to facilitate moving it from the closed to the open condition. Except for this difference, the construction shown in FIG. 8 is similar and operates similarly to the constructions described above.

FIG. 9 shows an embodiment wherein the closure member 90 has an adhesive layer on the lower surface thereof, and the adhesive is covered over by three separate members 92, 94 and 96. The members 92 and 94 are located to extend to adjacent opposite side edges 98 and 100 of the member 90 and the member 96 covers the adhesive in the area between the members 92 and 94. The construction shown in FIG. 9 can be made in any desired length or width and can be rolled up for storage as shown in FIG. 11 and unrolled so that the surgeon can cut off appropriate lengths as needed.

FIG. 10 shows the same device 90 shown in FIG. 9 in position wherein the non-adhesive cover layer 92 is being removed from the adhesive on the member 90 therebelow. The similar cover member 94 can also be removed in a similar manner as can the cover layer 96, if used. However, the cover layer 96 will usually remain in place until after the incision has been made and the surgical procedure completed. At that point, the surgeon can make up his mind whether he wants to adhesively reattach the portion of the adhesive layer covered by the member 96 or whether he prefers not to do that in the manner indicated above. The cover members 92, 94 and 96 each is shown having a tab 92A, 94A and 96A to make it easier to get a hold of them.

Figure 11:
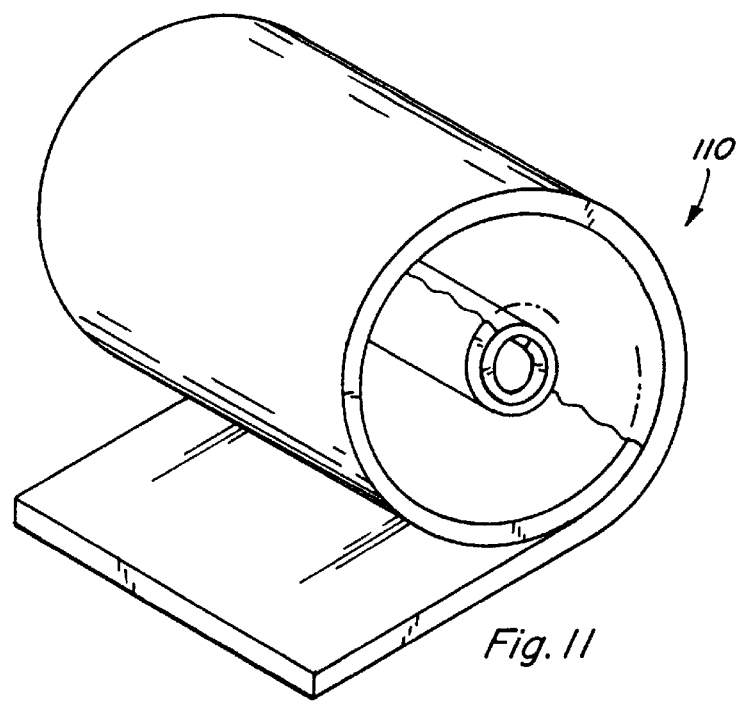
FIG. 11 shows a roll of the subject skin closure device which can be cut into lengths depending upon the needs of the particular surgical procedures to be performed.

FIG. 11 shows a roll 110 formed as described in connection with FIG. 9.

Figure 12:
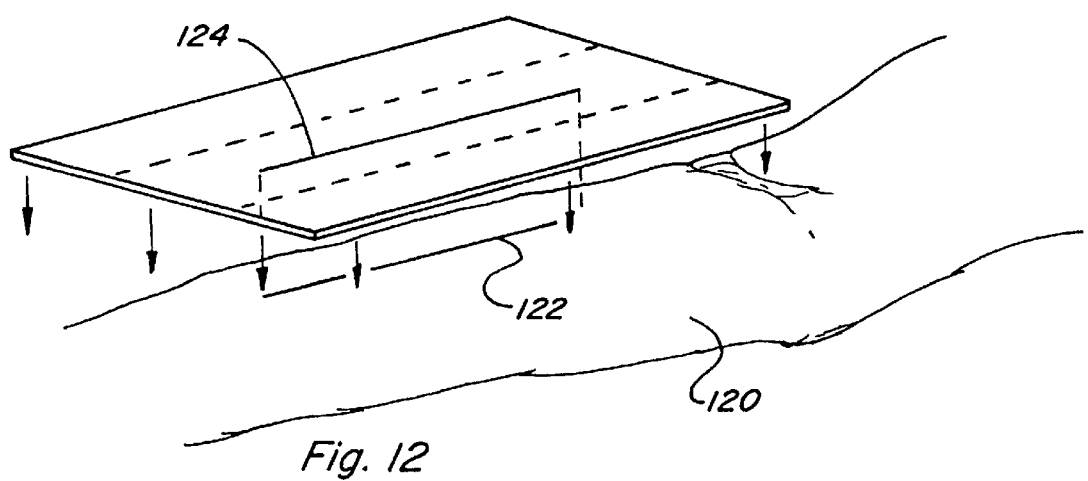
FIG. 12 is a perspective view showing the subject device located above an arm where an incision is to be made.

FIG. 12 shows a piece of the subject skin closure device located above an arm 120 which has a line 122 inscribed at the location where an incision is to be made. A similar line 124 is drawn or otherwise applied to the skin closure device at the location where the incision is to be made. If the closure device is formed of a transparent material, the lines 122 and 124 can be positioned in alignment with each other to facilitate installing the skin closure device in the desired position. Once this is done, the surgeon can make the incision through the device where the aligned lines 122 and 124 are positioned.

Figure 13:
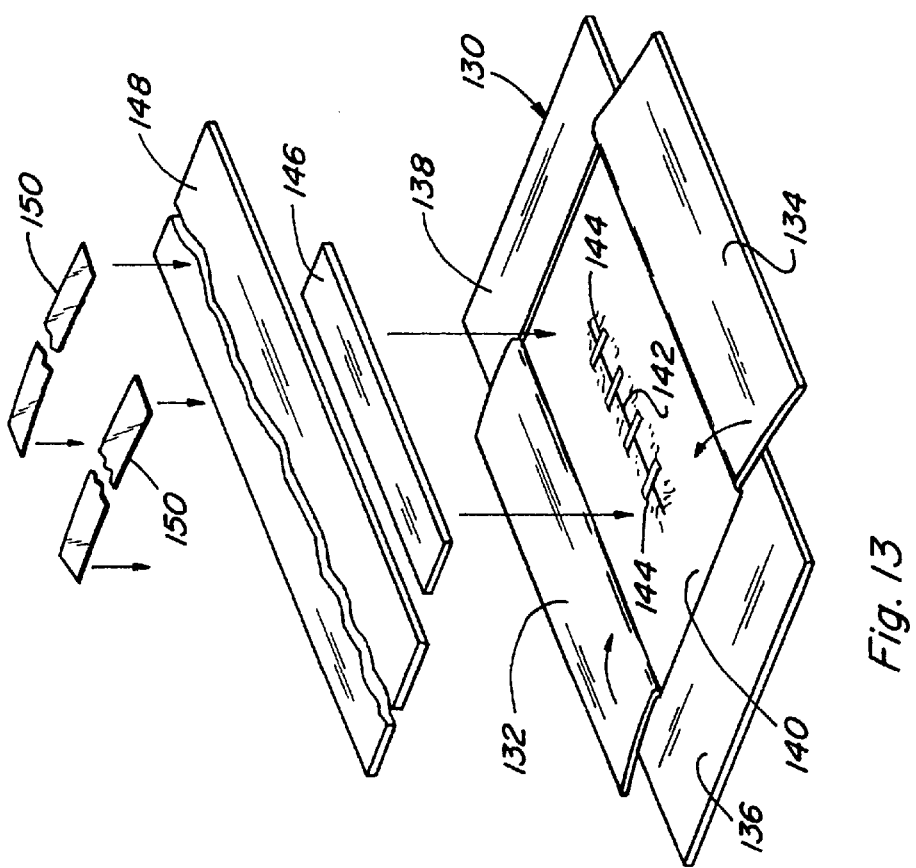
FIG. 13 is an exploded perspective view showing one embodiment of the subject skin closure device where the incision has been closed using surgical staples in readiness to receive a medication strip.

FIG. 13 is an exploded view showing an embodiment 130 of the subject device installed on the skin of a patient. The device as shown has two flaps 132 and 134 which are folded back. The flaps 132 and 134 are non adhesive or are covered with non adhesive cover layers. The device 130 also has connected end portions 136 and 138 which together with the inner edges of the flaps 132 and 134 define the area of the skin 140 where the incision 142 is located. The incision in this case is shown closed by surgical staples 144 which is possible with the present construction because there are no adhesive parts that extend up to the incision. The flaps 132 and 134 can be brought together and laid on the skin extending up to the incision 142. After this is done, a medication strip 146 can be placed on the closed flaps 132 and 134. The medication strip 146 can be adhesively attached or can be positioned and held in place as by placing a gauze member 148 thereover. If the gauze member 148 is used it can be attached and held in place by adhesive strips 150. It is also contemplated with the construction shown in FIG. 13 to hold the closed flaps 132 and 134 in a closed condition using elongated adhesive members 36 such as those described above.

Figure 14:
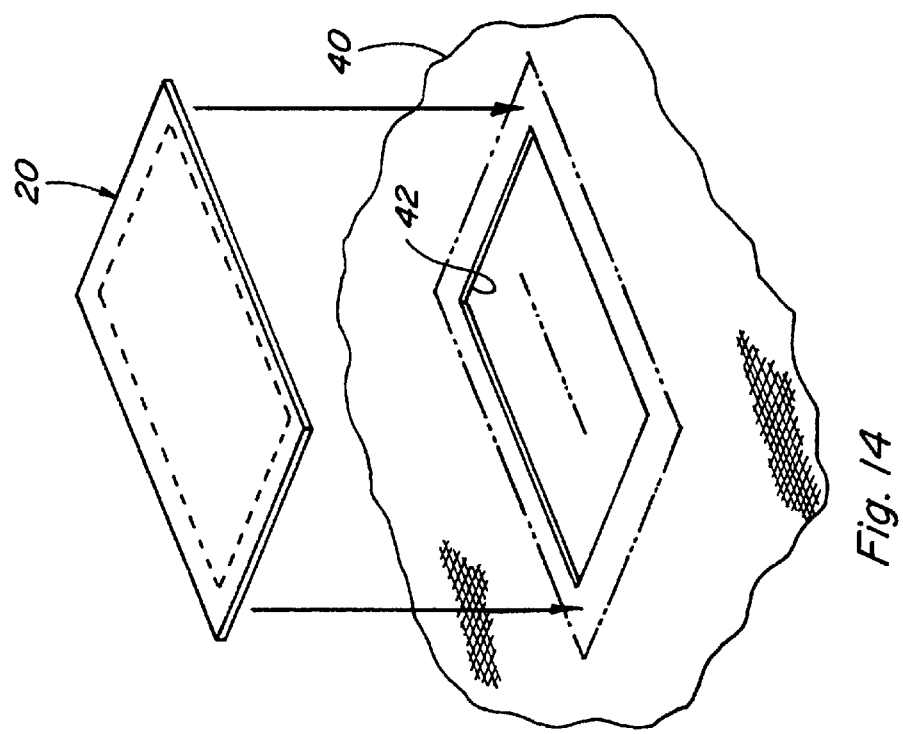
FIG. 14 is an exploded perspective view showing a portion of a surgical drape in position to receive a skin closure device.

FIG. 14 shows the subject device installed in the window 42 of the surgical drape 40. The desired form of the skin closure device is as described above. With this construction the skin closure device can be installed in the window prior to surgery after being marked up or otherwise prepared and can be removed from the window 42 at the conclusion of surgery whereby the skin closure device will remain attached to the body of the person who had the surgery and the drape 40 will be removed. The subject skin closure can be installed in the drape using the various means described above including zipper means, snap fasteners, VELCRO, hook and loop fasteners and it can be made integral with the drape and removed by cutting it around the periphery of the window at the desired time. It can also be attached along one or more sides of the window 42, as desired, using the desired attaching means.

Thus there has been shown and described several embodiments of a skin closure device which is flexible and provides the surgeon with many different options and advantages. The subject skin closure device also minimizes one of the problems with known devices, namely, the problem of having the skin closure device expand and contract at a different rate than the skin to which is it attached. This is accomplished with the present device by making the area adjacent to the incision non adhesive at least during the surgery although it may be made adhesive by removing cover flaps therefrom at the conclusion of surgery when there is no longer the problem of producing a stressed condition between the skin and the skin closure device.

What is claimed is:

1. A skin closure device comprising a flexible sheet of material having opposite side surfaces, spaced adhesive areas on one of the opposite side surfaces and a non adhesive area defined by and between the adhesive areas defining an area through which an incision is to be made leaving portions of the device adjacent opposite sides of the incision non adhesively attached to a patient's skin thereby enabling the non adhesively attached portions of the flexible sheet adjacent opposite sides of the incision to be raised outwardly from the skin and folded back exposing areas of the skin adjacent to opposite sides of the incision, said portions also able to be brought together along the incision, and at least one adhesive member for adhesively engaging and joining together the portions of the flexible sheet on opposite sides of the incision thereby closing the skin closure device along the incision and up to the edges of the incision.

2. The device of claim 1 including a flexible surgical drape having an opening located defining the area where the incision is to be made, the flexible sheet extending across the opening in the surgical drape.

3. The device of claim 1 wherein the at least one adhesive member includes a plurality of elongated members having adhesive extending along the length thereof.

4. The device of claim 1 wherein the flexible sheet has an adhesive over the entire surface of said one side surface and the non adhesive area of the flexible sheet includes a removable non adhesive member adhesively attached to said flexible sheet in the non adhesive area.

5. A skin closure device adapted to be used during surgical procedures comprising a flexible film of a material adapted to be placed on the skin of a person to be operated on in an area where a surgical procedure is to take place, said flexible film having an adhesive applied to one surface thereof, a pair of spaced removable layers of non-adhesive material attached to the adhesive flexible film and removable therefrom to enable attaching the flexible film to the skin of the person to be operated on, a second member formed of non-adhesive material attached to the flexible film and extending thereon along the region where an incision is to be made through the flexible member and into the skin whereby when an incision is made portions of the flexible film adjacent to the incision will not be adhesively attached to the skin, said portions extending along opposite sides of the incision and being movable to enable the adjacent portions of the flexible film to be folded back to positions to enable cleaning the skin and the skin closure member adjacent to the incision, said folded back portions also able to be brought together along the incision and at least one flexible member having an adhesive thereon for attaching to the flexible film on opposite sides of the incision to hold the film in a closed condition extending to the incision.

6. The device of claim 5 including a surgical drape having an opening therethrough to be located extending around the area where the incision is to be made, and means for attaching the flexible film to the drape in position extending across the opening whereby the drape can be removed when the surgical procedure has been completed while the skin closure member remains in position attached to the skin.

7. The device of claim 5 including a member capable of containing a quantity of a medication substance, an adhesive on said member for attaching it to the skin closure in position for seeping medication into the skin closure member and into the area around the incision to prevent infection from setting in.

8. In a surgical drape for covering a portion of the body of a patient to undergo surgery, the drape having an opening to be located in the area where the surgery is to be performed, the improvement including a device positioned extending across the opening for adhesively attaching to the body of the patient through which the surgery is to be performed, said device including a sheet of material adaptable to conform to the contour of the patient's body in the area of the surgery, said sheet having opposed surfaces one of which has spaced areas of an adhesive thereon for attaching the sheet to the body, a non adhesive area on said one surface where an incision is to be made whereby when an incision is made through the non adhesive area there will be portions of the non adhesive area on opposite sides of the incision that can be folded back to expose the skin adjacent to opposite sides of the incision said folded back portions also able to be brought together along the incision, and elongated members having an adhesive extending therealong for adhesively engaging the sheet member on opposite sides of the incision to hold the sheet member closed together on the body in position extending to both opposite edges of the incision without having the elongated members come in contact with the skin.

9. In a surgical drape of claim 8 means for attaching the device to the drape in position extending across the opening.

10. A skin closure device adapted to be used during surgical procedures comprising a flexible layer of a material adapted to be placed on a body in an area where a surgical procedure is to take place, said flexible layer of material have an adhesive on the surface thereof to be attached to the body, a first removable non adhesive member adhesively attached to the flexible layer of material in the area on the surface to be attached to the body, said first non adhesive member located in the area where an incision is to be made, a second removable non-adhesive layer of flexible material attached to the flexible layer of material and extending over the entire surface thereof and removable therefrom to enable the adhesive on the surface on opposite sides of the first non adhesive member to be attached to the body whereby, when an incision is made through the first non-adhesive member the portions thereof on opposite sides of the incision can be folded back exposing the skin on opposite sides of the incision, and adhesive strips each for attaching to the flexible layer of material in positions on opposite sides of the incision to hold the flexible layer of material and the body portions along the incision in substantially closed condition.

11. The skin closure device of claim 10 including an elongated porous member having a medication substance contained therein, said member attaching to the skin closure device in position extending along the incision whereby the medication substance is able to penetrate the area of the incision to reduce the possibility for infection.

12. The skin closure device of claim 10 including a surgical drape adapted to be positioned extending over the body to be surgically operated on, said drape having an opening therethrough located where the incision is to be made, and means for attaching the flexible layer of material to the drape and to the body to be operated on.

13. The skin closure device of claim 10 including a strip of flexible material attached to the flexible layer of material in the non adhesive area of the surface to be attached to the body.

14. The skin closure of claim 10 wherein the flexible layer of material is transparent.

15. The skin closure of claim 10 wherein the flexible layer of material is elongated and adaptable to be rolled up into a roll.

* * * * *